US005885432A

United States Patent [19]
Hooper et al.

[11] Patent Number: 5,885,432
[45] Date of Patent: Mar. 23, 1999

[54] UN-CROSSLINKED POLYMERIC MEDIA FOR ELECTROPHORESIS

[75] Inventors: Herbert H. Hooper, Belmont; Alexander P. Sassi, Berkeley; David S. Soane, Piedmont, all of Calif.; Young Bae, Seoul, Rep. of Korea

[73] Assignee: Soane BioSciences, Howard, Calif.

[21] Appl. No.: 589,150

[22] Filed: Jan. 22, 1996

Related U.S. Application Data

[63] Continuation-in-part of Ser. No. 477,652, Jun. 7, 1995, abandoned, which is a continuation of Ser. No. 241,048, May 10, 1994, Pat. No. 5,569,364, which is a continuation-in-part of Ser. No. 971,956, Nov. 5, 1992, abandoned.

[60] Provisional application No. 60/006,646 Nov. 10, 1995.

[51] Int. Cl.$^6$ ............... G01N 27/26; G01N 27/447
[52] U.S. Cl. ............... 204/469; 204/456; 204/606
[58] Field of Search ............... 204/455, 456, 204/457, 458, 459, 461, 462, 463, 464, 465, 466, 467, 468, 470, 605, 606, 607, 608, 609, 610

[56] References Cited

U.S. PATENT DOCUMENTS

| | | | |
|---|---|---|---|
| 4,894,250 | 1/1990 | Musson et al. | 426/573 |
| 4,952,686 | 8/1990 | Renn et al. | 536/114 |
| 5,057,560 | 10/1991 | Mueller | 524/22 |
| 5,104,954 | 4/1992 | Mueller | 526/307.7 |
| 5,230,832 | 7/1993 | Perlman | 204/468 |
| 5,631,337 | 5/1997 | Sassi et al. | 526/307.2 |

FOREIGN PATENT DOCUMENTS

WO 93/08200  4/1993  WIPO.

OTHER PUBLICATIONS

Heller, "Capillary Electrophoresis of Proteins and Nucleic Acids in Gels and Entangled Polymer Solutions," J. of Chromatography A (1995), 698:19–31.

Patil et al., "Synthesis of 2,3–Dihydroxypropyl Cellulose and its Polyacrylamide Graft Copolymers," Amer. Chem. Soc. (1986), 27:34–35.

Patil et al., "Synthesis and Characterization of Water–Soluble Polyacrylamide Graft Copolymers of Starch and 2,3–Dihydroxypropyl Cellulose," Polymer Materials, Science and Engineering (1986), 55:376–379.

Rempp and Franta, "Macromonomers: Synthesis, Characterization and Applications," Advances in Polymer Science (1984), 58:1–53.

Perlman et al., "Improved Resolution of DNA Fragments in Polysaccharide–Supplemented Agarose Gels," Analytical Biochemistry (1987), 163:247–254.

Perlman, "A Synergistic Gelling and Sieving Agent for Gel Electrophoresis in Normal and Low Melting Temperature Agarose," BioTechniques (1991), 11:754–756.

Bode, "The Use of Liquid Polyacrylamide in Electrophoresis 1. Mixed Gels Composed of Agar–Agar and Liquid Polyacrylamide," Analytical Biochemistry (1977), 83:204–210.

Horowitz et al., "Electrophoresis of Proteins and Nucleic Acids on Acrylamide–Agarose Gels Lacking Covalent Crosslinking," Analytical Biochemistry (1984), 143:333–340.

Warren et al., "Agarose–Acrylamide Gradient Gel Electrophoresis of Proteins," Analytical Biochemistry (1982), 121:331–334.

Peacock and Dingman, "Molecular Weight Estimation and Separation of Ribonucleic Acid by Electrophoresis in Agarose–Acrylamide Composite Gels," Biochemistry (1968), 7:668–674.

Schuller et al., "Electroimmunodiffusion of $\alpha_2$M, lgA and lgM in Manogram Quantities with a Hydroxyyethylcellulose–Agarose Gel: Application to Unconcentrated CSF," Clin. Chim. Acta (1972), 42:5–13.

Heller, "Capillary Electrophoresis of Proteins and Nucleic Acids in Gels and Entangled Polymer Solutions," J. of Chromatography A (1995), 2–13.

Kim and Morris, "Rapid Pulsed Field Capillary Electrophoretic Separation of Megabase Nucleic Acids," Anal. Chem. (1995), 67:784–786.

Barron et al., "Capillary Electrophoresis of DNA in Uncross–Linked Polymer Solutions," J. of Chromatography A. (1993), 652:3–16.

Baba et al., "High–Resolution Separation of DNA Restriction Fragments by Capillary Electrophoresis in Cellulose Derivative Solutions," J. of Chromatography A. (1993), 653:329–335.

Chen and Hoffman, "Graft Copolymers that Exhibit Temperature–Induced Phase Transitions Over a Wide Range of pH," Nature (Jan. 1995), 373:49–52.

Yoshida et al., "Comb–type Grafted Hydrogels with Rapid De–swelling Response to Temperature Changes," Nature (Mar. 1995), 374:240–242.

(List continued on next page.)

*Primary Examiner*—William H. Beisner
*Assistant Examiner*—John S. Starsiak, Jr.
*Attorney, Agent, or Firm*—Richard F. Trecartin; Flehr Hohbach Test Albritton & Herbert LLP

[57] ABSTRACT

Electrophoretic media are provided comprising at least un-crosslinked polymers which have a temperature reversible transition from low viscosity to high viscosity, so as to be pourable at one temperature, while providing sieving properties at another temperature. Optionally included with the un-crosslinked polymers having a reversible temperature responsive viscosity change are gelling agents and polymers which do not have the reversible temperature responsive viscosity change. The subject compositions have excellent clarity, provide excellent separation and resolution, handling properties, and mechanical strength. The compositions are compatible with transfer of separated components from the gel to an accepting membrane.

28 Claims, 3 Drawing Sheets

OTHER PUBLICATIONS deVos and Moller, "Polyacrylamide–Graft–Poly(Ethylene Oxide)," Makromol. Chem. Macromol. Symp. (1993), 75:223–229.

Yamaguchi, "Super–absorbent Polymers From Starch–Polyacrylonitrile Graft Copolymers by Acid Hydrolysis Before Saponification," Carbohydrate Polymers (1987), 7:71–82.

Ito et al., "Synthesis of Methyl Methacrylate–Stearyl Methacrylate Graft Copolymers and Characterization by Inverse Gas Chromatography," Macromolecules (Mar./Apr. 1980), 13:216–221.

Chatterji, "Glutaraldehyde Crosslinked Gelatin with Polyacrylamide Grafts," J. Macromol. Sci–Chem. (1990), 435–443. No Month Available.

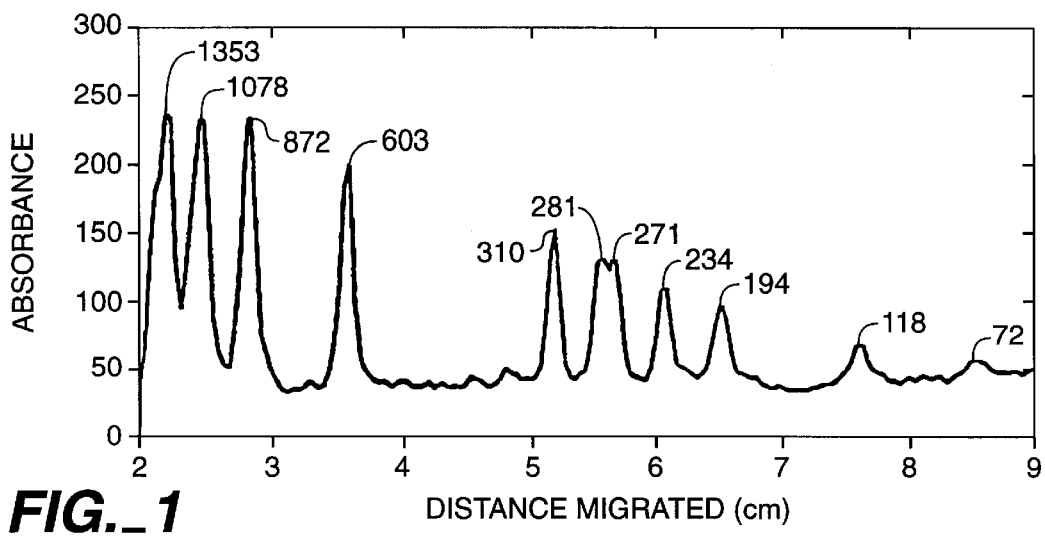
FIG._1
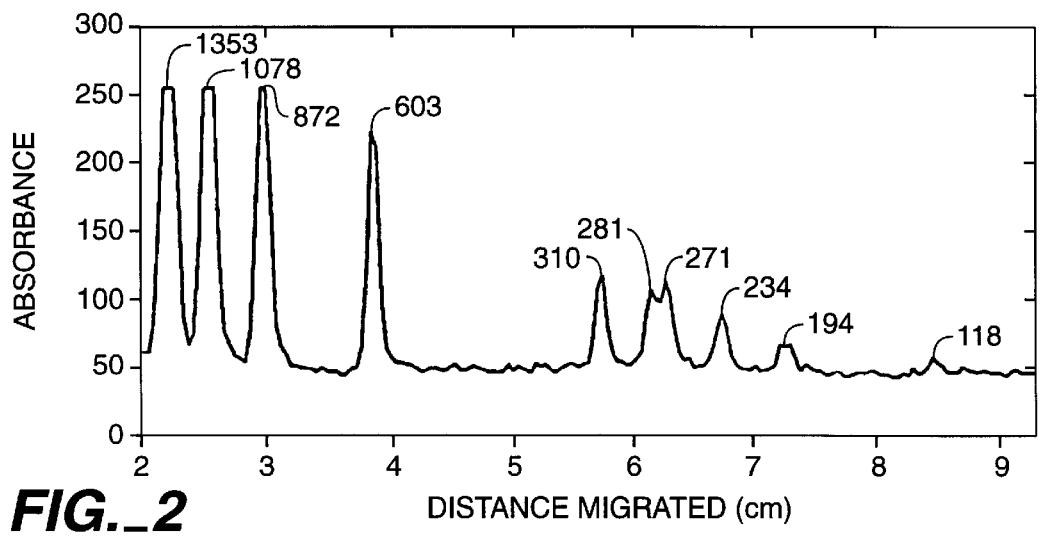
FIG._2
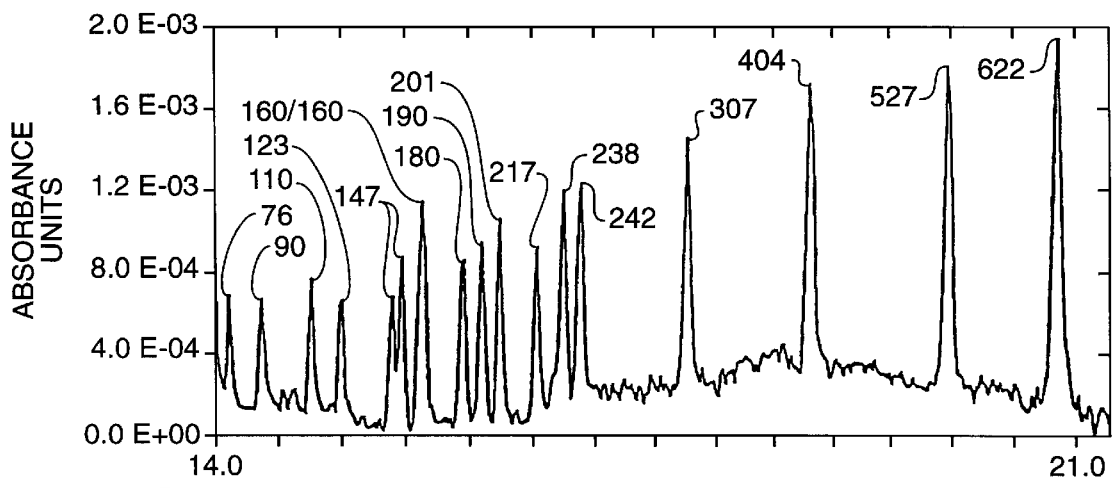
FIG._3

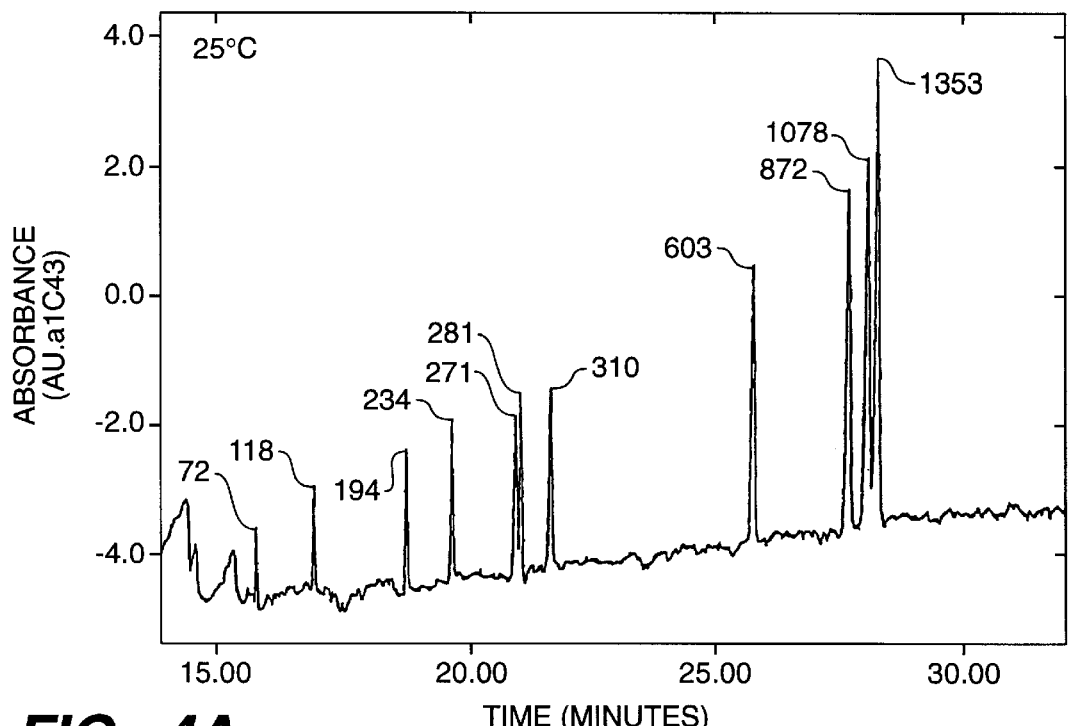
FIG._4A
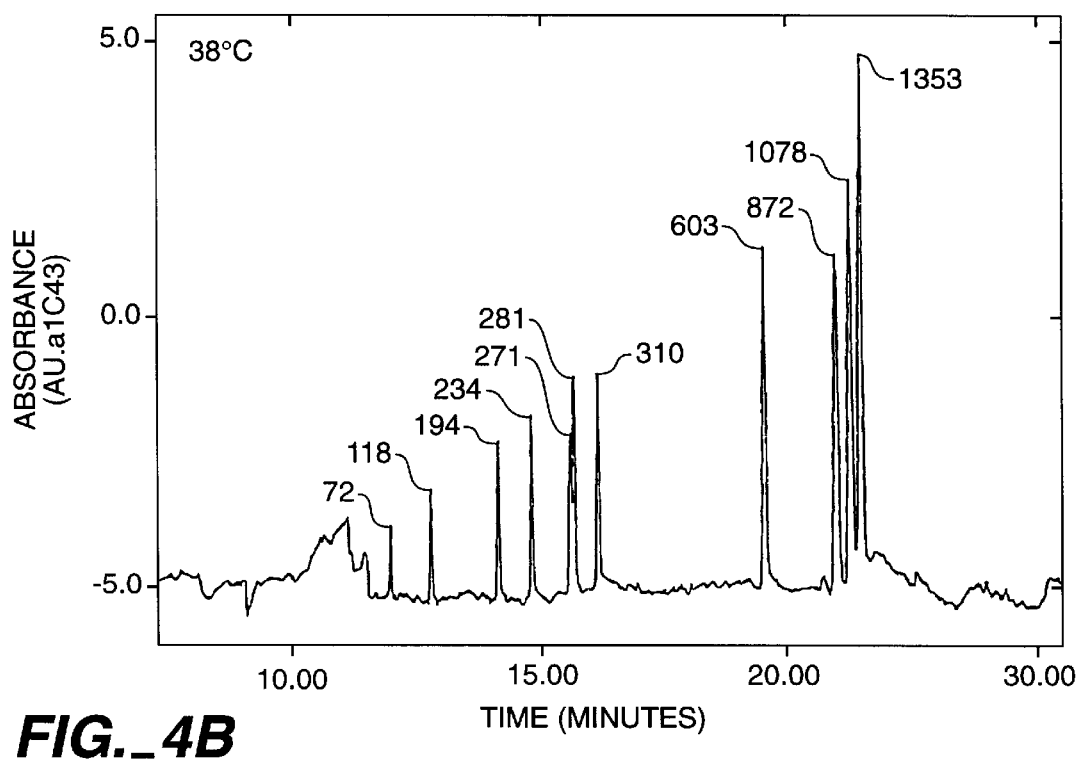
FIG._4B

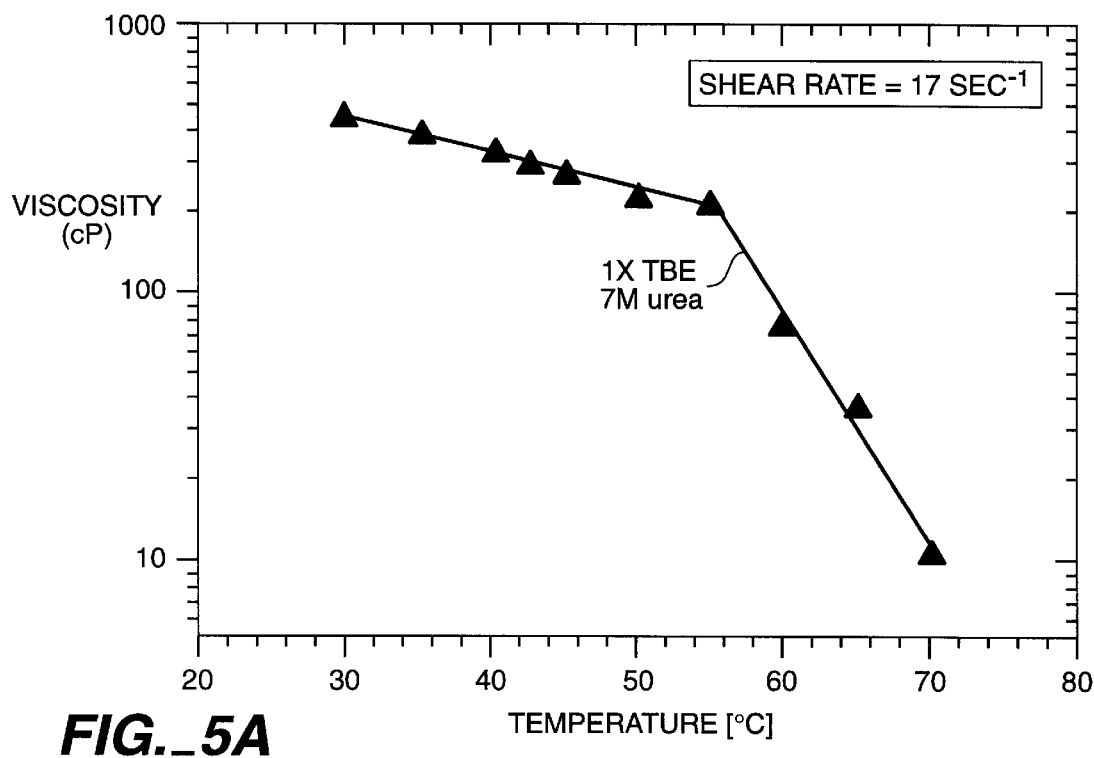
FIG._5A
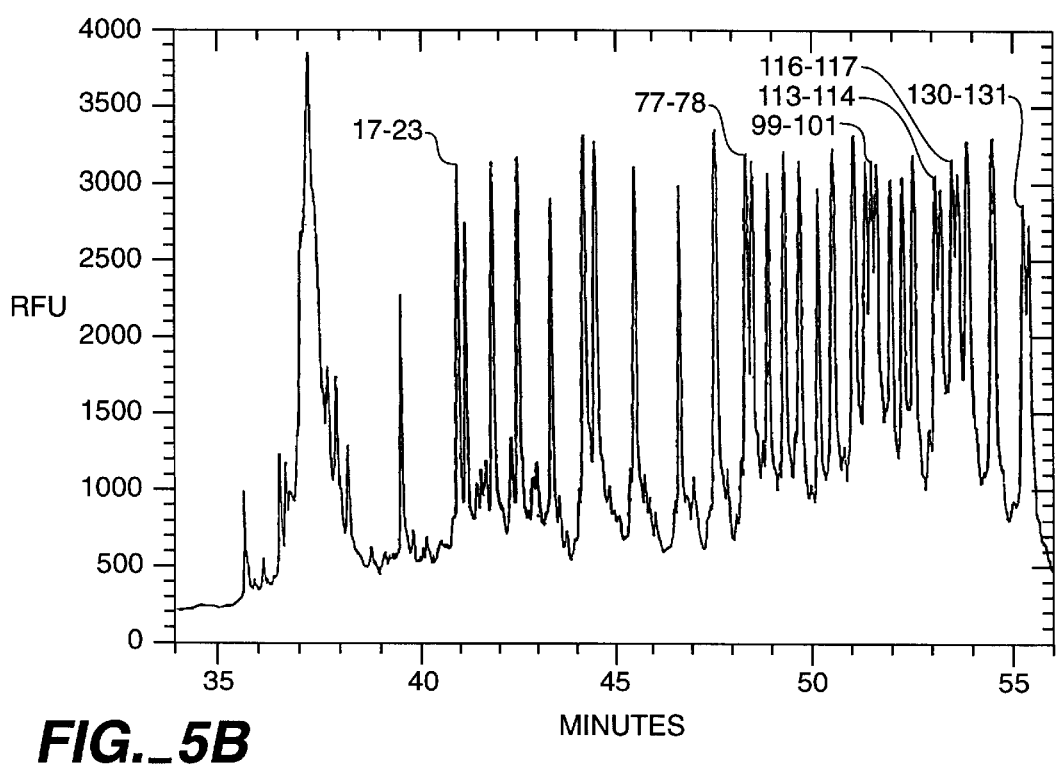
FIG._5B

UN-CROSSLINKED POLYMERIC MEDIA FOR ELECTROPHORESIS

CROSS-REFERENCES TO RELATED APPLICATIONS

This application claims the benefit of U.S. Provisional Application No. 60/006,646 filed Nov. 10, 1995 and a continuation in part of application Ser. No. 08/477,652, filed Jun. 7, 1995, now abandoned, which is a continuation of application Serial No. 08/241,048, filed May 10, 1994, now U.S. Pat. No. 5,569,364 Oct. 29, 1996 which is a continuation-in-part of application Ser. No. 07/971,956, filed Nov. 5, 1992, now abandoned.

BACKGROUND OF THE INVENTION

Gel electrophoresis is an extremely versatile tool with which to identify compounds associated with developments in biotechnology. Electrophoresis is used extensively for the separation, identification and preparation of pure samples of nucleic acids, polypeptides, and carbohydrates. In many applications, one wishes to separate components of a mixture, where the components may vary in relatively subtle ways. Separations may be associated with the detection of biomolecules (polypeptides, polynucleotides, polysaccharides, and combinations thereof, for example, glycosylated proteins, DNA-protein complexes) having different molecular characteristics, such as numbers of monomers, different sequences, different conformations, different charge/mass ratios, or different hydrophobicities/hydrophilicities. Essential to the success of the gel electrophoresis is the nature of the gel and the manner in which it is prepared.

The gel medium in electrophoresis serves one or more functions. For example, the medium can serve as an anticonvective support, a molecular sieve, a gradient of pH, or some other function. For the most part, two compositions dominate the gel compositions which are generally employed in slab gel formats: polyacrylamide and agarose. The polyacrylamides are normally crosslinked to provide for a sieving structure, where the proportion of crosslinking monomers determines the molecular weight range which may be separated by the gel. The addition polymers are normally formed in situ, where substantial care must be taken in the preparation of the gel to insure uniformity, substantial completion of the polymerization, and reproducibility of the separations achieved on the gel. For agarose, the source of agarose is a naturally occurring material, so there can be great variation in the quality of the agarose, the nature of the contaminants, and the like. Therefore, there is substantial uncertainty in going from one batch to another batch of agarose whether one is obtaining gels of comparable quality.

While the polyacrylamides used in slab gel electrophoresis are normally crosslinked, this crosslinking is not required for molecular sieving, but rather for providing anticonvective and mechanical properties to the medium. By contrast, in capillary electrophoresis, mechanical integrity and anticonvective properties are not requirements of the gel medium and un-crosslinked solutions are commonly used for their molecular sieving properties. Barron (1995) reviews the prior art with respect to the large variety of un-crosslinked polymer solutions that have been used in capillary electrophoresis, including hydroxyethylcellulose, polyacrylamide, and various other polymers. Un-crosslinked polymers have been used in slab gel electrophoresis when the un-crosslinked polymer is contained in a composite matrix with agarose. In this manner, the agarose contributes mechanical and anticonvective properties, and prevents the un-crosslinked polymer from dissolving into the surrounding buffer. Examples include combinations of un-crosslinked polyacrylamide and agarose (Bode et al.) and combinations of hydroxyethylcellulose and agarose (Perlman et al.).

Major shortcomings remain in current methods of using un-crosslinked polymers in capillary and slab gel electrophoresis. Even moderate concentration solutions of high molecular mass polymers are very viscous, and difficult to load in narrow bore capillaries or to pour in slab gel chambers. The viscosity of un-crosslinked polyacrylamide in aqueous solution demonstrates a log-linear temperature profile, i.e. the log of the viscosity decreases linearly with temperature. This behavior is typical of hydrophilic polymers, and is found in solutions of hydroxyethylcellulose, polyethylene oxide and other hydrophilic, water-soluble polymers. Thus, the viscosity of these solutions is reduced by an equal percentage for every unit increase in temperature, thereby requiring large temperature increases to obtain sufficient viscosity reduction.

The preparation and formation of the gel is not simple and there are many problems in insuring that bubble formation does not occur, that there are no hot spots, and there is homogeneity. While filling a slab gel is an art form, filling a capillary for capillary electrophoresis is a matter of greater complexity. Furthermore, despite the complexity and difficulties in preparing the gels, both slab and capillary, one may only be able to use the gel once and then have to discard it. This means that a substantial proportion of time for obtaining the result from gel electrophoresis is involved with the preparation of the gel.

One of the reasons there are so few materials which have found acceptance for gels is the relatively large number of parameters which the gels must fulfill. Included among these parameters are excellent resolution, handling properties, optical clarity, mechanical strength, ease of transfer of separated sample to other substrates, acceptance of various reagents for binding to or reacting with the bands of the sample, and ease of recovery of the sample. To retain all of these characteristics at a high performance level while still improving other characteristics, such as ease of forming the gel slab or gel containing electrophoretic capillary and ease of handling during the formation of the gels in the holder, has proved to be extremely elusive.

Alternative compositions to those described above have been suggested such as combinations of agarose and galactomannan (U.S. Pat. No. 5,230,832), modified cellulose (Perlman et al. *Anal. Biochem.* 163:247–254 (1987)), water soluble gums (U.S. Pat. No. 4,290,911; 4,894,250; and 4,952,686), and 1,3-glucans (WO 93/08200). Hydroxyethylcellulose has been suggested for use in capillary electrophoresis (Barron et al. *J. Chromatography A*, 652:3–16 (1993)). Entangled polymer solutions for capillary electrophoresis have been described in Heller, *J. Chromatography A*, V710N2 (1995) 309–32 1.

SUMMARY OF THE INVENTION

Electrophoretic device components, methods, and compositions for use in such components are provided, where the compositions comprise un-crosslinked high molecular weight polymers having a reversible temperature responsive viscosity change in polar solutions. The un-crosslinked polymers may be used by themselves or in conjunction with non-temperature sensitive un-crosslinked polymers, crosslinked polymers or gelling agents. In response to a relatively narrow temperature change, the compositions go from a low viscosity, pourable state to a high viscosity, sieving state for electrophoresis. The compositions find use in various electrophoretic gel configurations, such as slab gels, capillaries and microchannels.

The methods taught here comprise adjusting the temperature such that the composition is on the low viscosity side of the transition during loading into the device, and then changing the temperature such that the composition is on the high viscosity side of the transition during separation. This method, which has not been previously taught to our knowledge, can be practiced with any compositions that undergo a reversible viscosity transition of the type described herein. Exemplary compositions are provided, but the generality of the method is such that it may be practiced with a wide variety of similar or different compositions that exhibit the requisite viscosity responsiveness. General rules for identifying families of such compositions are taught, wherein the method taught here can be applied with these other compositions.

BRIEF DESCRIPTION OF THE FIGURES

FIG. 1 is an electropherogram illustrating the results of the separation of ΦX174-Hae III DNA fragments in a slab gel composite matrix of agarose, HPC and HEC.

FIG. 2 is an electropherogram illustrating the results of the separation of ΦX174-Hae III DNA fragments in a slab gel composite matrix of agarose, linear poly DMA/DEA and HEC.

FIG. 3 is an electropherogram illustrating separation of pBR322/Msp I DNA fragments by capillary electrophoresis in a composite matrix of HEC and HPC, as described in Example 7.

FIGS. 4a & 4b are electropherograms showing the separation of (ΦX174-Hae III DNA fragments by capillary electrophoresis in a composite matrix of HEC and HPC at 25° and 38° C., as described in Example 8.

FIGS. 5a provides a viscosity profile for a media comprising a synthetic, temperature sensitive un-crosslinked polymer, while FIG. 5b is an electropherogram of M13mp18 fragments by capillary electrophoresis in the media, as described in Example 9.

DESCRIPTION OF THE SPECIFIC EMBODIMENTS

Improved devices, compositions and methods are provided for performing gel electrophoresis. Preparing gels for electrophoresis is substantially simplified by employing as the sieving composition un-crosslinked high molecular weight polymers, which polymers may be synthetic, naturally occurring, or modified naturally occurring polymers. The polymers may be addition polymers, condensation polymers, homo polymers, co-polymers, block, random, or graft polymers, and the like. The un-crosslinked polymers may be used by themselves or in conjunction with crosslinked polymers or gelling agents.

The polymers will, for the most part, provide a viscosity at a temperature in the range of about 20° to 50° C. at a weight % concentration of 0.25 to 20%, more usually 0.5 to 10%, of from about 1 to 100,000 cP, usually 1 to 50,000 cP, more usually 5 to 10,000 cP. At these concentrations, the media may be used for complete filling of the gel or matrix holder of the device in which the media are employed. The media comprise a continuous fluid phase. In the high viscosity state, the media will have at least a 100% greater viscosity than the media in the low viscosity state. Usually, the viscosity in the high viscosity state will be at least about 100 cP, more usually at least about 750 cP, generally at least about 1,000 cP, and the viscosity may be as high as 5 million cP or higher, where the media becomes a solid, elastic gel-like solid mass that is no longer flowable, pourable, or pumpable.

The media will comprise a continuous fluid phase, normally comprising a, polar solvent, preferably an aqueous polar solvent, where the amount of water would generally range from about 10–100%. The media may comprise various organic polar solvents, such as ethanol, dimethylformamide, hexamethylphosphoramide, acetonitrile, diethylether, dimethyl sulfoxide, etc. Generally, the co-solvents will be present in less than about 90 volume percent, more usually less than about 50 volume percent, particularly less than about 25 volume percent. Also included in the media may be various salts, particularly buffering salts, where the concentration of the salts will vary from about 0.01 to 0.5, more usually 0.01 to 0.1M. The salts may include Tris, phosphate, EDTA, borate, acetate, MOPS, etc. The pH may vary widely, generally being in the range of about 2 to 10, more usually in the range of about 5 to 9.

The un-crosslinked polymers which provide for temperature responsive viscosity changes may be varied widely as to their composition. The un-crosslinked polymer may be a natural or synthetic homopolymer, random copolymer, multi-block copolymer, grafted copolymer of a linear, branch or comb-like structure, and the like. A number of thermoreversible un-crosslinked polymers have been reported in the literature. (By "thermoreversible" is intended a polymer which in a polar, usually aqueous, medium is able to go from a pourable solution to a high viscosity medium through a narrow, usually less than 20° C., more usually in the range of about 10° to 15° C., temperature change.) Some of these thermoreversible polymers have now been found to have sieving properties at high viscosity. Among naturally occurring polymers which have been modified or derivatized are modified celluloses, such as hydroxyalkyl celluloses where alkyl is of from 2 to 4, usually 2 to 3 carbon atoms, which may have been further modified by alkylation of the cellulose with an alkyl group of from 1 to 3 carbon atoms, usually 1 to 2 carbon atoms. Illustrative compositions include ethylhydroxyethylcellulose, hydroxypropyl cellulose, hydroxypropyl methyl cellulose, etc. These derivatized naturally occurring polymers have molecular weight ranges in the range of about 75 to 500 kD. Naturally occurring polysaccharides include tamarind seed polysaccharides, and the like.

Various addition polymers may be employed, prepared from a wide variety of derivatized acrylamide (includes methacrylamide) monomers, where the derivatives are present on the amide nitrogen. Substituents on the nitrogen include adamantyl; glycinyl; benzyl; cyclohexyl; diethyl; dodecyl; 3-methoxypropyl; ethoxyethyl; tetrahydrofurfuryl; isobornyl; dimethyl; diacetonyl; 3-(diethylamino)propyl; methyl; and 1-naphthylmethyl. Generally, the substituents will range from about 1 to 12 carbon atoms, more usually from about 1 to 8 carbon atoms, may be aliphatic, alicyclic, aromatic, heterocyclic, or combinations thereof, substituted or unsubstituted, generally be substituted with oxygen or nitrogen, as oxy, oxo or amino. Of particular interest are copolymers of N,N-dialkyl acrylamides, where the alkyl groups are of from 1 to 5, usually 1 to 3 carbon atoms, more particularly where the alkyl groups on a nitrogen atom are the same. Other polymers which may be used include polyvinyl alcohols.

The addition polymers may be prepared by any convenient polymerization technique which affords the desired minimum molecular weight of at least about 30 kD, more usually at least about 100 kD, and maybe up to 5,000 kD or more, as a number average molecular weight. Conveniently, free radical polymerization is carried out in appropriate diluent, where the monomer(s) are dissolved in an appropriate media, such as water, aqueous/organic, or organic medium. Polymerization is initiated using initiators appropriate for the monomer and medium, e.g. ammonium persulfate/TMED, ammonium persulfate/sodium metabisulfate in aqueous media, azoisobutyronitrile in organic media, and the like. In preparing the polymer, the monomers are dissolved in the medium of choice in conjunction with the initiator and stirred. When necessary, oxygen may be removed from the solution prior to initiation of the reaction by means such as vacuum degassing, bubbling a stream of nitrogen or helium through the medium, or the like. The resultant molecular weight will be influenced by the concentration of initiator, temperature of reaction, choice of diluent and concentration of monomer. The resulting polymers may be purified with extensive dialysis against pure water and subsequently recovered by conventional drying methods, such as freeze-drying, spray drying, film-drying, roll-drying, precipitation and the like, followed by washing.

Graft copolymers of two distinct polymers may be employed as the un-crosslinked polymer, where a first polymer forms a scaffolding structure and a second polymer, engrafted onto the first polymer, reversibly changes its structure or orientation with respect to the first polymer in response to an applied stimulus. An exemplary graft polymer would be one in which a first or scaffolding polymer forms a structure of large pores with minimal sieving capability. The second or switchable polymer would be engrafted onto the first polymer so that in the first state prior to application of the stimulus, the engrafted second polymer strands would align adjacent to the first polymer thereby occupying a minimal portion of the pores of the first polymer. Upon application of the stimulus, the second polymer changes position so as to occupy a substantial portion of the pores of the first polymer, thereby significantly changing the sieving properties of the graft polymer medium. In this embodiment, the first or scaffolding polymer that provides a structure to the media would generally be one which reversibly changes from a first to a second state at a different applied stimulus from the stimulus which causes the second, engrafted polymer to transition from the first to the second state. For example, one could have the first polymer which is flowable at a first elevated temperature and forms a solid, porous matrix at a second temperature. Over the range of temperatures at which the first polymer sets into the gel like state, the second, engrafted polymer could change position, thereby filling the pores of the first polymer and changing the sieving properties of the media. Thus, by modulating the temperature further to the point where the engrafted polymer changes position relative to the first polymer, the engrafted polymer may then change position so as to substantially fill the pores of the first polymer. The change in position of the engrafted polymer may be proportional to the change in temperature, providing for control over the degree of filling of the pore size of the media and the possibility of dynamically changing the pore size of the media, as will be discussed further below. Illustrative graft co-polymers having temperature reversible viscosity changes include N-isopropyl acrylamide grafted with acrylic acid, poly(oxyethylene), poly (hydroxyethylmethacrylate), and the like (see Rempt and Franta, *Advances in Polymer Science* 58, Springer-Berleg. 1984, *Macromonomers: Synthesis, Characterization, and Applications*; Chen and Hoffman (1995) *Nature* 373:49–52; de Vos and Moller, *Makromol. Chem., Macromol. Symp.* 75:223–229 (1993)).

Combinations of the various un-crosslinked thermoreversible polymers may be employed where 2 or more, usually not more than 4, may be used in a single composition. Each of the component polymers may vary from about 5 to 95 weight % of the total polymer composition. Where 2 polymers are used, the amount of each polymer will be in the range of about 5 to 95, usually from about 15 to 85, more usually from about 20 to 80, and often from about 25 to 75 weight % of the total polymer composition.

Combinations of the various un-crosslinked temperature sensitive polymers with various un-crosslinked, non-temperature sensitive polymers may be employed where two or more, usually not more that eight, different polymer may be present in a single composition. Non-temperature sensitive polymers of interest include homopolymers and copolymers of both synthetic and natural origin. The un-crosslinked non-temperature sensitive polymers may be derivatized, branched, grafted and the like. Specific un-crosslinked non-temperature sensitive polymers of interest include polyacrylamide, polyvinylpyrrolidone, polyvinyl alcohol, hydroxyethylcellulose, and the like. Each of the component polymers may vary from about 5 to 95 weight percent of the total polymer composition. Where two or more polymers are present in combination, the amount of each polymer will be in the range of about 5 to 95, usually from about 15 to 85, more usually from about 20 to 80, and often from about 25 to 75 weight % of the total polymer composition.

The media containing only the un-crosslinked temperature sensitive polymers may not form a gel. To form a gel other additives may be provided which provide for gelation.

Gelling or binding agents which may be present in the media in conjunction with the thermoreversible un-crosslinked polymer may be any natural, synthetic or derivatized natural substance which, in combination with the un-crosslinked polymer, does not interfere with the temperature reversible viscosity change, nor the sieving properties of the gel. The total concentration of the un-crosslinked polymer and gelling agent will generally be at least about 0.1 and not more than about 25 weight percent, preferably not more than about 10 weight percent of the hydrated gel. The total concentration of the gelling agent will generally be in the range of about 0.1 to 25 weight percent, preferably not more than about 10 weight percent, usually not more than about 5 weight percent of the hydrated gel.

Binding or gelling agents may include agar, agarose, carrageenan, curdlan, gelatin, polyacrylylglycinamide, polymethacrylylglycinamide, tamarind seed polysaccharide, or the like, where the gelling agent may have a viscosity profile which is temperature sensitive or non-temperature sensitive, as temperature sensitive is defined above.

The binding or gelling agent may be introduced by mixing with the viscosity temperature responsive un-crosslinked polymer during preparation of the electrophoresis medium or by soaking the medium contained in a permeable mold in a solution of the binding agent.

The subject media may also comprise the un-crosslinked temperature sensitive polymers in conjunction with a crosslinked polymer. In these media compositions, the crosslinked polymer will form large pores in which the temperature sensitive un-crosslinked polymers are entrapped, i.e. the crosslinked polymer serves as a framework for the un-crosslinked temperature sensitive polymers. Media comprising un-crosslinked temperature sensitive polymers entrapped in a crosslinked polymer framework provide for the possibility of dynamic porosity during electrophoresis, as described in greater detail below. Specific crosslinked polymers that may be included in the media to provide a framework for the un-crosslinked temperature sensitive polymers include: crosslinked polyacrylamide, and the like. To prepare media comprising temperature sensitive un-crosslinked polymers in conjunction with a cross-linked polymer(s), the crosslinked polymeric framework can be synthesized in a solution of the temperature sensitive, un-crosslinked polymer(s).

In addition to the other components, the media according to the subject invention may include surfactants, stabilizers, denaturants, and the like.

Included among the electrophoretic devices in which the subject media find use are slab devices, column devices, microchannel devices, capillary devices, and the like. By virtue of the subject invention, gels may be pre-prepared or safely prepared by the end user. Therefore, for the most part, where the gels are to be pre-cast, the gels will have the sieving high viscosity characteristic at room temperature.

In preparing and using electrophoretic devices according to the subject invention, the first step is the introduction of the medium into the gel holder of the device. The medium will be introduced into the gel holder in the first state of low viscosity. Since the medium is readily pourable and flowable in the first state, it will fill the gel holder without voids, bubbles, or other irregularities.

Following introduction of the medium into the gel holder, by providing for a temperature change which results in the transition of the media from the first to the second state, the medium will then be in a state for electrophoresis. The stimulus may be applied using any convenient heating or cooling means. With the gel in the second state, electrophoresis of the sample in the device may then be carried out by introducing the sample into the gel medium and applying a sufficient voltage gradient across the gel. The buffers employed and the subject gels may be used in accordance with conventional techniques used for other electrophoretic gels, such as crosslinked polyacrylamide and agarose. Any sample amenable to electrophoresis may be employed, where the sample may comprise a single or plurality of components. Samples employed for separation or identification may include nucleic acids, proteins, carbohydrates, combinations thereof, under naturing or denaturing conditions. If desired, following electrophoresis, the medium may be returned to the first state of low viscosity through application of the appropriate stimulus, for removal from the electrophoretic device, and other processing.

Although the subject media are suitable for use in any electrophoretic device comprising a gel holder, the media are particularly applicable for use in slab, capillary or microchannel gel electrophoresis devices.

In preparing a capillary for gel electrophoresis, the medium is first introduced into the separation chamber or interior space of a capillary using any convenient means, such as injection or suction by vacuum where the medium is in the first state of low viscosity. Once the medium is introduced into the capillary, the medium is converted into the second state of high viscosity to provide a sievable composition. Electrophoresis of the sample may then be performed.

During electrophoresis, the medium may be maintained in a constant state, so as to provide for constant sieving characteristics during electrophoresis of the sample. Alternatively, the conditions of the media may be modulated during electrophoresis, thereby changing the sieving properties of the media. Thus, one can provide for dynamic sieving conditions during electrophoresis, where the sieving conditions may be optimized for a particular sample to achieve more efficient resolution of the separated sample compounds over the course of the electrophoretic run. For example, a first set of conditions may be employed and the sample partially separated. After partial separation, the conditions may be changed, whereby more defined separation may be obtained. One may use stepwise changing of the conditions or gradual dynamic changing of the conditions. For example, one could apply a temperature gradient to the medium, where the temperature of the medium gradually changes over time, so that the pore size and sieving capability of the media gradually changes at a defined rate during electrophoresis. In this way, a temporal gradient can be achieved, thereby providing for optimum separation conditions for the various sample components of the medium. The magnitude of temperature change used to achieve dynamic porosity in the medium will generally range from about 1° to 70 ° C., usually from about 5° to 50 ° C., more usually from about 5 to 20 ° C., where the temperature modulation will usually take place over a period of minutes to hours depending on the time scale of the preparation.

The gel may be reused, depending upon the nature of the sample which had been employed. Where the gel is to be discarded, the capillary can be easily flushed free of medium by changing the medium conditions back to the low viscosity first condition under which the capillary was filled.

Employing the subject compositions provides for a number of advantages. Improved homogeneity of gels is achieved, where the gels are free of defects. The varying properties with temperature of the gels allows for modulation of the conditions of the separation during the electrophoresis. Also, by modulating the characteristics of the gel, one may remove components from the gel following the electrophoretic separation, so that the gel medium may be reused for subsequent separations. For example, one may modify the gel from the high viscosity second state to an intermediate lower viscosity state, so that upon application of a sufficient voltage gradient across the gel, substantially all of the separated sample components may be run through the gel.

The subject gels provide for good separation of both large and small sample components. Separations can be achieved which are the equivalent of gels comprising approximately 3.5 to 10% w/v polyacrylamide and 3.33% crosslinking. For slab gel electrophoresis, good resolution is obtained with differences of ten nucleotides with nucleotides with dsDNA having from 10 to 300 bp.

The following examples are offered by way of illustration and not by way of limitation.

EXPERIMENTAL

Sources for cited chemicals:

| | |
|---|---|
| Hydroxyethylcellulose (HEC) | Polysciences, Hercules |
| Hydroxypropylcellulose (HPC) | Scientific Polymer Products, Aldrich |
| Ethylhydroxyethylcellulose(EHEC) | Akzo Nobel (Sweden) |
| Agarose | Bio-Rad, Hispanagar (Spain), Ina Food Industries (Japan) |
| Ammonium Persulfate (APS) | Sigma |
| N,N,N',N' tetramethylethylenediamine (TEMED) | Sigma |
| Dimethylacrylamide (DMA) | Polysciences, Monomer-Polymer Dajac |
| Diethylacrylamide (DEA) | Polysciences, Monomer-Polymer Dajac |
| Ethidium bromide (EtBr) | Bio-Rad |
| Ethylcellulose (EC) | Sigma |
| 1,1,1 - Trichloroethane (TCE) | Aldrich |
| Pluronic P105 | BASF Performance Chemicals |
| Methylenebisacrylamide (BIS) | JT Baker, Sigma |

EXAMPLE 1
Preparation of un-crosslinked polymer

N,N'-dimethylacrylamide and N,N'-diethylacrylamide were used to synthesize linear poly-DMA/DEA(50/50). The solution was prepared at 8% T where: % T=(grams of DMA+grams of DEA)/total volume in mL·100. A solution was prepared containing 1.6 g DMA, 1.6 g DEA and 36.8 g deionized distilled water. Nitrogen was bubbled for 1 hour through the solution while stirring. To the solution was then added rapidly 90 μL of 20 weight percent ammonium persulfate and 40 mL of TEMED. The bottle was sealed and stirring was continued for an additional 30 seconds. The bottle was then transferred to a refrigerator at 9° C. and the reaction allowed to proceed for 48 hours.

At the end of this time, the viscous solution was transferred to dialysis tubing (12,000 MW cutoff) and dialyzed in a five-gallon tank containing deionized distilled water. The water was changed daily for three days to ensure removal of unreacted monomer and low molecular weight oligomers. After dialysis, the solution was transferred to freeze-dry in a flask and frozen at −20° C. The polymer was freeze dried for four days under a vacuum of 0.04 mbar. The resulting polymer was a low density foam-like material which could be readily dissolved in an aqueous medium to provide the subject compositions.

EXAMPLE 2
Viscosity Transition of a Derivatized Natural Polymer with Temperature Sensitivity 0.4 g of EHEC (Bermocoll E320F) was added to 18.5 deionized, distilled water and 1.05 g 10×TBE buffer. Using a magnetic stir bar, the solution was stirred until the EHEC dissolved. Viscosity was measured as a function of temperature using a Brookfield DV-II+ viscometer. The viscosity was measured at different shear rates by changing the rpm of the spindle (Spindle #31).

0.4 g of HPC (MW 300,000) was added to 18.5 g deionized, distilled water and one g 10×TBE buffer. Using a magnetic stir bar, the solution was stirred until the HPC dissolved. Viscosity was measured as before.

There are three main regions apparent in a plot of the temperature dependence of the log of viscosity for a solution of temperature sensitive polymer: two regions of steady decline, and one intervening region of sharp decline. The overall shape of the log viscosity/temperature curve is sigmoidal.

As the temperature is increased, the viscosity decreases, as is expected for solutions of non-temperature sensitive polymers. A gradual, linear dependence is observed for the temperature-dependence of the log of solution viscosity until the transition temperature. Near the transition temperature (approximately 42° C. for HPC, 65° C. for EHEC), the log of the solution viscosity declines sharply and dramatically. Above the transition temperature, the log of the viscosity continues to decline, but again in a gradual, linear manner as before.

EXAMPLE 3
Viscosity Transition of a Composite Formulation Containing Temperature-Sensitive Polymer 3a. Combinations of temperature sensitive and non-temperature sensitive un-crosslinked polymers.

0.75 g of HEC (MW 90,000–105,000) and 0.75 g of HPC (MW 300,000) were dissolved in 98.5 g of 0.5×TBE by vigorous manual shaking followed by turning the solution overnight. 0.75 g of HEC and 0.75 g of HPC were dissolved in 0.5 ×TBE, 7M urea by the same method.

One gram of HEC (MW 90,000–105,000) and one gram of HPC (MW 300,000) were dissolved in 98 g of 1.0 ×TAE by vigorous manual shaking followed by turning the solution overnight. Viscosity was measured as before, with results analogous to those observed in Example 2.

3b. Combinations of temperature sensitive and non-temperature sensitive un-crosslinked polymers with a gelling agent.

0.2 g HEC (MW 90,000–105,000), 0.2 g HPC (MW 300,000) and 0.1 g agarose were mixed and added to 18.5 g deionized, distilled water and one g 10×TBE buffer. Using a magnetic stir bar, we dissolved the HEC and HPC. Viscosity was measured upon heating and subsequent cooling at a spindle rotation of three rpm using the Brookfield DV-II+ viscometer.

When heated, the viscosity behavior for solutions containing un-crosslinked temperature sensitive polymers and un-crosslinked non-temperature sensitive polymers in combination with a gelling agent is similar to that for solutions containing only un-crosslinked polymers which do not gel, as described in Example 2. When cooled from high temperatures, the viscosity of media containing a gelling agent or binding agent such as agarose increases gradually until the vicinity of the transition temperature (42° C. in this example), whereupon the viscosity increases sharply and dramatically with further cooling. If the gelling or binding agent is present in sufficient quantity, such as in this example, the solution will gel, and the viscosity will become effectively infinite.

EXAMPLE 4
Slab Gel Electrophoresis of dsDNA fragments in a Composite Matrix Containing agarose, a derivatized Natural Polymer with Temperature Sensitivity, and a Non-Temperature Sensitive Polymer One gram HEC (MW 90,000–105,000) and one gram HPC (MW 300,000) were added to 5 g 10×TBE buffer and 92.5 g deionized, distilled water. Before adding 0.5 g agarose, the solution was stirred until the HEC and HPC were dissolved. The solution was heated in a boiling water bath to dissolve the agarose, and ethidium bromide was added to the matrix to a concentration of 1 µg/mL. The solution was allowed to cool to approximately 55° C. before pouring into a 15 by 20 cm casting tray. Electrophoresis was run for 2 hours at 5.8 V/cm in 0.5×TBE buffer. DNA samples (from left to right in the gel) were: 10 bp ladder, pBR322/MSP I, 100 bp ladder, (ΦX174/Hae III, 10 bp ladder, pBR322/Msp I, (ΦX174/Hae III, and 100 bp ladder.

The resultant gel gave good resolution of the DNA fragments. The 10 bp ladder was resolved up to 150 bp, and the 100 bp ladder was resolved completely (100–1500 bp). All of the (ΦX174/HaeIII fragments were resolved (72, 118, 194, 234, 271, 281, 310, 603, 872, 1078, and 1353 bp), See FIG. 1, and all of the pBR322/Msp I fragments were resolved (67, 76, 90, 110, 123, 147, 160, 180, 190, 201, 217, 242/238, 307, 404, 527, 622 bp) except that the 238 and 242-bp fragments appeared as one band.

In a second experiment, 2.5 grams of a blend containing equal parts of HEC (MW 90,000–105,000), HPC (MW 60,000) and agarose were added to 97.5 g 0.5×TBE buffer which had been pre-chilled to about 10° C. The solution was stirred for 20 minutes using a magnetic stir-bar. The solution was then heated in a boiling water bath to dissolve the agarose for about 10 minutes. The solution was cooled to about 60° C. and ethidium bromide was added to a concentration of 0.5 µg/mL. The solution was further cooled to about 38° C. before pouring. The gel was allowed to set at room temperature for 20 minutes and placed in a refrigerator for an additional 40 minutes. The following samples were loaded onto the gel: 10 bp ladder, 100 bp ladder, (ΦX174/HaeIII, and pBR322/MspI. Electrophoresis was run for 4 hours at 5.8 V/cm in 0.5×TBE buffer prechilled to 10° C.

The resultant gel gave excellent resolution of the DNA fragments. All samples were resolved, including the 238 and 242 bp fragments of the pBR322/Msp I digest.

EXAMPLE 5
Slab Gel Electrophoresis of dsDNA fragments in a Composite Matrix Containing agarose, a Synthetic, Temperature-Sensitive Polymer, and a Non-Temperature Sensitive Polymer Similar to Example 1, 1.598 g DMA and 1.609 g DEA were added to 36.8 g deionized, distilled water. Nitrogen was bubbled through the monomer solution for approximately 2 hours while stirring. 90 µL of a 20 wt % ammonium persulfate and 40 µL of TEMED were added, and the solution was stirred quickly. Polymerization was allowed to occur for one day in a refrigerator at 9° C. Ten grams of the resulting polymer solution of un-crosslinked temperature sensitive polymer was added to 64.8 g deionized, distilled water, 4 g 10×TBE, and 0.8 g HEC. The solution was stirred to dissolve the HEC (MW 90,000–105,000) and dilute the un-crosslinked polymer. After the addition of 0.4 g agarose, the solution was heated with stirring to dissolve the agarose. Ethidium bromide was added to the solution to a final concentration of 0.5 µg/mL. The solution was allowed to cool to approximately 60° C. before pouring into a 15 by 20 cm casting tray (Hoefer). Electrophoresis was run for 2 hours at 5.8 V/cm in 0.5×TBE buffer. DNA samples (from left to right) are: pBR322/Msp I ,100 bp ladder, (ΦX174/Hae III fragment, 10 bp ladder, 10 bp ladder, 100 bp ladder, ΦX74/Hae III, and pBR322/Msp I.

The resultant gel gave good resolution. The 10 bp ladder was resolved up to 150 bp, and the 100 bp ladder was resolved completely (100–1500 bp). All of the ΦX174HaeIII fragments were resolved (72, 118, 194, 234, 271, 281, 310, 603, 872, 1078, and 1353 bp), See FIG. 2, and all of the pBR322/Msp I fragments were resolved (67, 76, 90, 110, 123, 147, 160, 180, 190, 201, 217, 242/238, 307, 404, 527, 622 bp) except that the 238 and 242- bp fragments appeared as one band.

EXAMPLE 6
Capillary Electrophoresis of dsDNA Fragments in a Solution Containing Temperature-Sensitive Polymer One gram of EHEC was dissolved in 0.5×TBE buffer by vigorous manual shaking followed by turning overnight. A 57-cm capillary was pressure loaded with the EHEC solution at 350 psi. The 75-micron-ID capillary was coated with polyacrylamide following the procedures described by Hjertén (Hjertén, 1985). DNA fragments (ΦX174/Hae III) were loaded electrokinetically for 20 seconds at 10 kV. Electrophoresis was performed using a Beckman P/ACE System 2100 at 14 kV. DNA was detected via absorbance at 260 nm. All fragments were resolved except for the 271 and 281 bp-fragments, which appeared as one peak on the electropherogram.

One gram of HPC (MW 300,000) was dissolved in 1×TBE by vigorous manual shaking followed by turning overnight. A 57.5-cm capillary was pressure-loaded with the HPC solution at 350 psi. The 75-micron-ID capillary was coated with polyacrylamide following the procedure of Hjertén (Hjertén 1985). DNA fragments of (ΦX174/HaeIII were loaded electrokinetically for four seconds at 10 kV. Electrophoresis was performed using a Beckman P/ACE System 2100 at 15 kV.

All fragments were resolved except for the 271 and 281 bp-fragments, which appeared as one peak on the electropherogram.

EXAMPLE 7
Capillary Electrophoresis of dsDNA Fragments in a Solution Containing Temperature-Sensitive and Non-Temperature-Sensitive Polymer 0.4 g of HEC (MW 90,000–105,000) and 1.5 g of HPC (MW 300,000) were dissolved in 98.1 g of 0.5×TBE by vigorous manual shaking followed by turning overnight. A 57-cm capillary was pressure-loaded with the HEC/HPC solution at 350 psi. The 75-micron-ID capillary was coated with polyacrylamide following the procedure of Hjertén (Hjertén, 1985). DNA fragments of pBR322/MspI were loaded electrokinetically for seven seconds at 10 kV. Electrophoresis was performed using a Beckman P/ACE System 2100 at 14 kV. Excellent resolution of all fragments was obtained, including the two 147-bp fragments which differ only in sequence. See FIG. 3.

EXAMPLE 8
Capillary Electrophoresis of dsDNA Fragments in a Solution Containing Temperature-Sensitive and Non-Temperature-Sensitive Polymer at two different temperatures 1.25 g HEC (MW 90–105,000) and 0.25 g HPC (MW 300,000) were dissolved in 98.5 g 1×TBE by vigorous manual shaking followed by turning overnight. A 57 cm capillary was pressure loaded with the HEC/HPC solution at 350 psi. The 75 micron ID capillary was coated with polyacrylamide following the procedure of Hjertén (Hjertén, 1985). FIG. 4a is an electropherogram for a run conducted at 25° C. FIG. 4b is an electropherogram for a run conducted at 38° C. DNA fragments of ΦX174/HaeIII were loaded electrokinetically for 10 seconds (FIG. 4a) or 7 seconds (FIG. 4b) at 10 kV. Electrophoresis was performed using a Beckman P/ACE System 2100 at 11 kV.

In this matrix, both large and small DNA fragments are separable at 25 and 38° C. However, smaller fragments are resolved better at 25° C. than at 38° C., and the 1078 bp/1353 bp fragments are resolved slightly better at 38° C. Plots of selectivity versus temperature show that the selectivity of the matrix for large and for small fragments depends on temperature, demonstrating the dynamic porosity behavior of the media.

EXAMPLE 9

Capillary Electrophoresis in a Separation Medium Comprising a Temperature Sensitive Synthetic Un-crosslinked Polymer N,N-diethylacrylamide and N,N-dimethylacrylamide were used to synthesize linear poly-DMA/DEA (30/70). The solution was prepared at 6% T. A solution was prepared containing 7.2 g DMA, 16.8 g DEA and 376 mL deionized distilled water. Helium was bubbled for 1 hour through the solution while stirring. To the solution was added rapidly 320 μl of 20 weight percent ammonium persulfate and 320 μl of TEMED. The bottle was sealed and stirring continued slowly at room temperature for 30 minutes. The bottle was then transferred to a refrigerator at 4° C. and the reaction was allowed to proceed for 24 hours. At the end of this time, the viscous solution was transferred to dialysis tubing (6–8,000 MW cutoff) and dialyzed in a five gallon tank for three days to ensure removal of unreacted monomer and low molecular weight oligomers. After dialysis, the polymer solution was transferred to a freeze-drying flask and placed in a freezer for 48 hours. The frozen polymer solution was then lyophilized for three days. The resulting dried polymer was redissolved in 1×TBE, 7M urea at a concentration of 6 weight percent.

The viscosity of the 6 weight % solution of DEA/DMA copolymer was measured as a function of temperature using a Brookfield DVII+ viscometer as before. Viscosity data is shown in FIG. 5a. The viscosity transition occurs in the vicinity of 55° C. for this preparation.

A 70 cm, 75 micron inner diameter, polyacrylamide coated capillary was pressure loaded at 50 psi. DNA from an M13mp18 sequencing reaction for T-terminated fragments was loaded electrokinetically for 15 second at 12 kV. Fragments were prepared via primer extension using the Sequanase Sequencing Kit (Amersham Life Science). Electrophoresis was performed at 12 kV using a Beckman P/ACE System 2100, and the results are shown in FIG. 5b. Single-base resolution was obtained up to 150 bases, demonstrating the feasibility of this type of temperature sensitive matrix for DNA sequencing.

It is evident from the above description that the subject invention provides for greatly improved applications for gel electrophoresis, by providing for gels which can be readily pre-cast, easily loaded, even into microchannels and capillaries, and provide for excellent separation, even of closely related sample components. The gel may then be removed by changing the temperature to the pourable state and the gel removed. Being able to change the viscosity also allows for ease of separation of the components being separated. The subject gels provide for excellent clarity, handling properties and, as needed, mechanical strength.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An electrophoretic device comprising an electrophoretic gel holder containing an electrophoretic medium in a capillary or microchannel, said medium comprising a component consisting essentially of an un-crosslinked thermoreversible acrylamide copolymer containing a derivatized acrylamide in an amount sufficient to provide in said medium over a range of temperatures less than 20° C. a transition between a first state and a second state wherein said medium has a viscosity in said second state at least 100% higher than in said first state.

2. An electrophoretic device according to claim 1, wherein said acrylamide copolymer is a copolymer of N,N-dialkyl acrylamides.

3. An electrophoretic device according to claim 1, wherein said medium is in a first state at a temperature in the range of about 20° to 50° C., and wherein said viscosity in said first state is in the range of about 1 to 100,000 cP.

4. An electrophoretic device according to claim 1, wherein said medium further comprises a non-temperature sensitive un-crosslinked polymer.

5. An electrophoretic device according to claim 1, wherein said medium further comprises a crosslinked polymer.

6. An electrophoretic device according to claim 1, wherein said medium further comprises not more than about 10 weight percent of a gelling agent.

7. An electrophoretic device according to claim 6, wherein said gelling agent is agarose.

8. An electrophoretic device according to claim 1, wherein said acrylamide copolymer is a copolymer of N,N-dialkyl substituted acrylamide.

9. An electrophoretic device according to claim 1 wherein said transition between said first and second states is provided over a range of temperatures less than 10° C.

10. An electrophoretic device according to claim 1 wherein said acrylamide polymer is present in said medium at a concentration between 0.25 weight percent and 20 weight percent.

11. An electrophoretic device according to claim 10 wherein said acrylamide polymer is present in said medium at a concentration between 0.5 weight percent and 10 weight percent.

12. An electrophoretic device comprising an electrophoretic gel holder containing an electrophoretic medium, said medium comprising an un-crosslinked thermoreversible derivatized cellulose in an amount sufficient to provide in said medium over a range of temperatures less than 20° C. a transition between a first state and a second state wherein said medium has a viscosity in said second state at least 100% higher than in said first state.

13. An electrophoretic device according to claim 12, wherein said at least one derivatized cellulose is hydroxyethyl cellulose, hydroxypropyl cellulose or ethylhydroxyethylcellulose.

14. An electrophoretic device according to claim 12, wherein said at least one derivatized cellulose has a molecular weight range in the range of about 75,000 to 500,00 kD and is ethylhydroxyethylcellulose or a combination of hydroxyethylcellulose and hydroxypropylcellulose.

15. An electrophoretic device according to claim 12 wherein said transition between said first and second states is provided over a range of temperatures less than 10° C.

16. An electrophoretic device according to claim 12 wherein said derivatized cellulose is present in said medium at a concentration between 0.25 weight percent and 20 weight percent.

17. An electrophoretic device according to claim 16 wherein said derivatized cellulose is present in said medium at a concentration between 0.5 weight percent and 10 weight percent.

18. An electrophoresis device according to claim 12, wherein said medium is in said first state at a temperature in the range of about 20° to 50° C., and wherein said viscosity in said first state is in the range of about 1 to 100,000 cP.

19. The device of claim 12 wherein said medium comprises two or more derivatized celluloses.

20. In a method for carrying out an electrophoretic separation of a sample, the improvement which comprises steps of:

providing a device according to claim 1, said medium being at a temperature at which said medium is in said second state, introducing the sample into said medium, and applying a voltage gradient across said medium sufficient to effect movement in said medium of at least one component of the sample.

21. The method according to claim 20, further comprising the step of modulating the said temperature of said medium during said movement of said component in said medium.

22. A method for preparing an electrophoretic device for electrophoretic separation of a sample, comprising steps of:

providing an electrophoretic gel holder comprising a capillary or microchannel, providing an electrophoretic medium comprising a component which consists essentially of an un-crosslinked thermoreversible derivatized cellulose or an acrylamide copolymer containing a derivatized acrylamide in an amount sufficient to provide in said medium over a range of temperatures less than 20° C. a transition between a first state and a second state wherein said medium has a viscosity in said second state at least 100% higher than in said first state, introducing said medium into said electrophoretic gel holder at a temperature at which said medium is in a said first state, and changing the temperature of said medium in said electrophoretic gel holder to a temperature at which said medium is in said second state.

23. The method of claim 22 wherein said component is a derivatized acrylamide copolymer.

24. The method of claim 23 wherein said copolymer is a copolymer of N,N-dialkyl acrylamides.

25. The method of claim 22 wherein said component is a derivatized cellulose.

26. The method of claim 25 wherein said derivatized cellulose is hydroxyethyl cellulose, hydroxypropyl cellulose or ethylhydroxyethylcellulose.

27. The method of claim 25 wherein said component comprises two or more derivatized celluloses.

28. An electrophoretic device according to claim 22 wherein said transition between said first and second states is provided over a range of temperatures less than 10° C.

* * * * *